United States Patent
Tamai

(10) Patent No.: US 11,850,409 B2
(45) Date of Patent: Dec. 26, 2023

(54) MEDICAL NEEDLE

(71) Applicant: KAWASUMI LABORATORIES, INC., Saiki (JP)

(72) Inventor: Yusuke Tamai, Bungo-ono (JP)

(73) Assignee: KAWASUMI LABORATORIES, INC., Saiki (JP)

( * ) Notice: Subject to any disclaimer, the term of this patent is extended or adjusted under 35 U.S.C. 154(b) by 228 days.

(21) Appl. No.: 17/235,469

(22) Filed: Apr. 20, 2021

(65) Prior Publication Data

US 2021/0330894 A1 Oct. 28, 2021

Related U.S. Application Data

(60) Provisional application No. 63/014,541, filed on Apr. 23, 2020, provisional application No. 63/014,528, filed on Apr. 23, 2020.

(51) Int. Cl.
*A61M 5/32* (2006.01)
*A61M 25/06* (2006.01)

(52) U.S. Cl.
CPC ....... *A61M 5/3245* (2013.01); *A61M 25/0637* (2013.01)

(58) Field of Classification Search
None
See application file for complete search history.

(56) References Cited

U.S. PATENT DOCUMENTS

| | | | | |
|---|---|---|---|---|
| 4,747,831 A * | 5/1988 | Kulli | ................. | A61M 25/0631 604/110 |
| 5,817,058 A * | 10/1998 | Shaw | ................ | A61M 25/0631 604/110 |
| 6,193,690 B1 * | 2/2001 | Dysarz | .............. | A61M 25/0631 604/110 |
| 6,210,371 B1 | 4/2001 | Shaw | | |
| 6,530,903 B2 * | 3/2003 | Wang | .................... | A61M 5/322 604/110 |
| 7,097,633 B2 * | 8/2006 | Botich | ............. | A61B 5/150366 604/110 |
| 7,846,135 B2 * | 12/2010 | Runfola | .............. | A61M 5/3234 604/110 |
| 8,496,600 B2 * | 7/2013 | Shaw | ............... | A61B 5/150259 604/110 |
| 8,597,241 B2 * | 12/2013 | Yang | ................. | A61M 25/0631 604/110 |

(Continued)

FOREIGN PATENT DOCUMENTS

JP 2002-539897 11/2002

*Primary Examiner* — Theodore J Stigell
(74) *Attorney, Agent, or Firm* — Womble Bond Dickinson (US) LLP

(57) ABSTRACT

A medical needle includes a needle portion (10) having a needle tip on a distal end, a case (30) configured to be capable of accommodating the needle portion that can be exposed from the distal end side, a movement mechanism (50) for moving the needle portion inside the case, and a movement restricting portion (37) that restricts the needle tip accommodated in the case from moving in a direction opposite to a moving direction of the needle portion. The movement restricting portion maintains the needle tip accommodated in the case such that the needle tip can come into contact with an inner face of the case to restrict the movement of the needle tip in the opposite direction.

7 Claims, 10 Drawing Sheets

(56) References Cited

U.S. PATENT DOCUMENTS

| | | | |
|---|---|---|---|
| 2004/0267200 A1* | 12/2004 | Carlyon | A61M 25/0631 604/110 |
| 2005/0038385 A1* | 2/2005 | Shen | A61M 5/322 604/110 |
| 2009/0131872 A1* | 5/2009 | Popov | A61M 25/0631 604/164.08 |
| 2020/0289792 A1* | 9/2020 | De Zolt | A61M 5/3232 |

* cited by examiner

MEDICAL NEEDLE

CROSS REFERENCE TO RELATED APPLICATIONS

This application claims priority under 35 U.S.C. 119 to U.S. provisional patent applications 63/014,541 and 63/014,528, filed Apr. 23, 2020. The entire teachings of the above application are incorporated herein by reference.

TECHNICAL FIELD

The present invention relates to a medical needle.

BACKGROUND ART

As a medical needle used for blood collection, blood transfusion, fluid infusion, or the like, a medical needle in which a spring member is disposed inside a cylindrical case has been conventionally known (e.g. see JP 2002-539897 W). According to the conventional medical needle, a needle tip exposed from a case can be accommodated in a case by an action of a spring member. Thus, it is possible to prevent occurrence of an accident that one who uses the medical needle (including a medical worker and a patient, who are hereinafter referred to as a user) accidentally sticks a used medical needle into oneself (so-called erroneous sticking).

SUMMARY OF THE INVENTION

After a needle tip is accommodated in a case, this state can be maintained by an action of a spring 60, but if the action of the spring 60 is lost due to an external impact or the like, the needle tip may be exposed from the case again. Thus, it is desirable to prevent occurrence of erroneous sticking also after the accommodation.

Also, in the conventional medical needle, a spring having a relatively strong repulsive force is occasionally used as a spring member to securely put a needle tip into a case. In this case, the needle or a needle connection portion accommodated in the case energetically comes into contact with an inner face of the case, and accordingly a relatively strong impact and a collision noise occur, so that a user may have a discomfort feeling.

The first object of the present invention is to keep the needle tip accommodated in the case, to be maintained in the case.

The second object is to alleviate a user's discomfort feeling caused when a needle tip is accommodated in a case.

A medical needle according to an aspect of the present invention includes a needle portion having a needle tip on a distal end, a case configured to be capable of exposing the needle portion to the distal end side and accommodating the needle portion, a movement mechanism for moving the needle portion inside the case until the needle tip protruding from the case is accommodated in the case, and a movement restricting portion that restricts the needle tip accommodated in the case from moving in a direction opposite to a moving direction of the needle portion by the movement mechanism, wherein the movement restricting portion maintains the needle tip accommodated in the case such that the needle tip can come into contact with an inner face of the case, to restrict movement of the needle tip in the opposite direction.

A medical needle according to an aspect of the present invention includes a needle portion having a needle tip on a distal end, a case configured to be capable of exposing the needle portion to the distal end side and accommodating the needle portion, a movement mechanism for moving the needle portion inside the case until the needle tip protruding from the case is accommodated in the case, and a movement restricting portion that restricts the needle tip accommodated in the case from moving in a direction opposite to a moving direction of the needle portion by the movement mechanism, wherein the case includes a base portion having a hole portion through which the needle tip can pass and a cover portion for closing an opening on the opposite side to the hole portion of the base portion, and the movement restricting portion engages a part of at least either the movement mechanism or the needle portion with an engaged part of the cover portion to restrict the movement of the needle tip in the opposite direction.

DESCRIPTION OF THE PREFERRED EMBODIMENTS

Hereinafter, embodiments of the medical needle according to the present invention will be explained with reference to the figures. According to the embodiments, the first object can be achieved.

Embodiment 1-1

Figure 1:
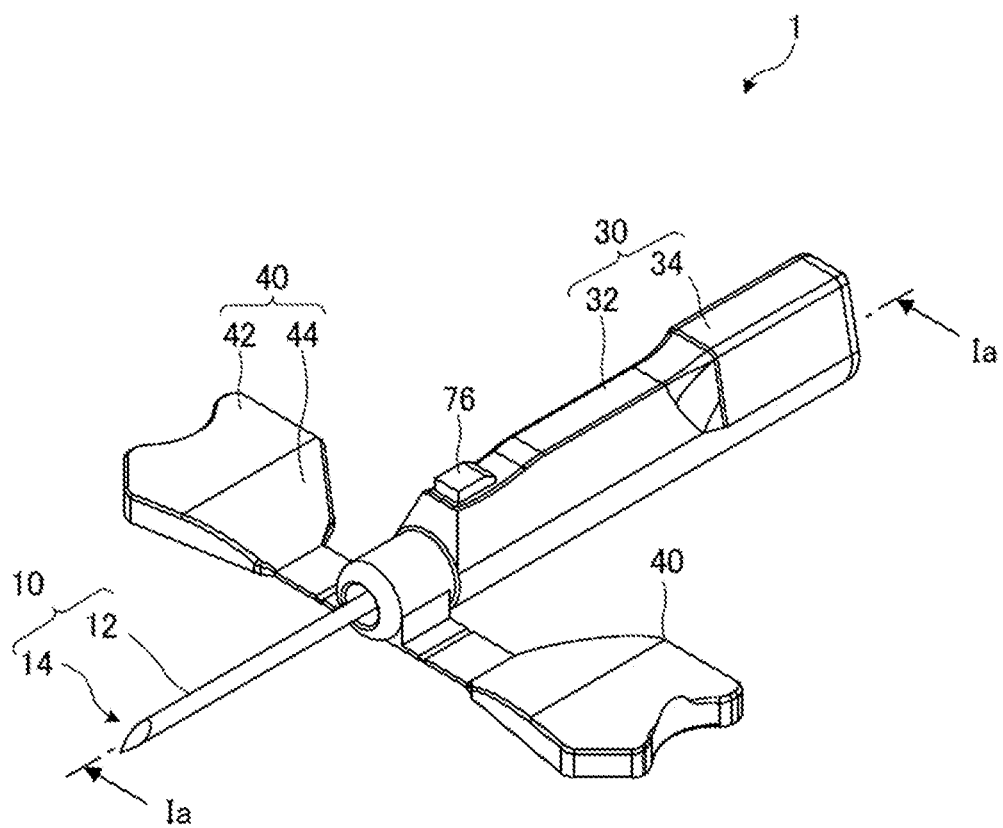
FIG. 1 is an overall perspective view of a medical needle according to embodiment 1-1.
Figure 2:
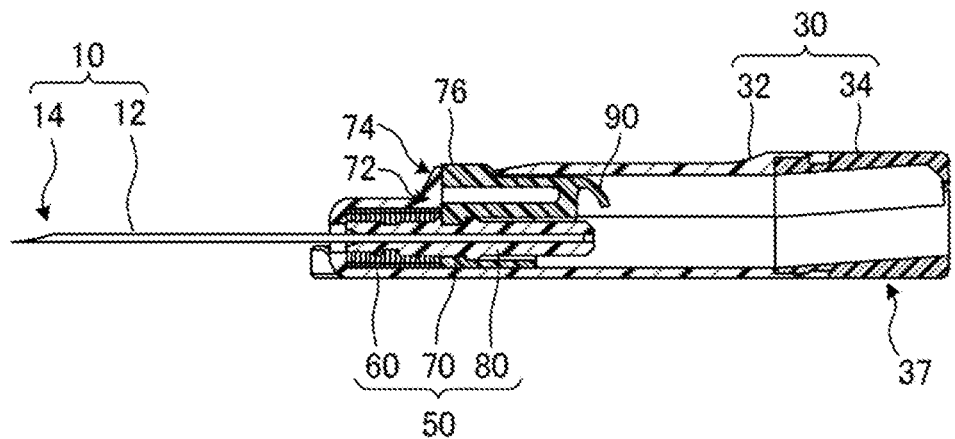
FIG. 2 is a sectional view taken along line Ia-Ia in FIG. 1.
Figure 3:
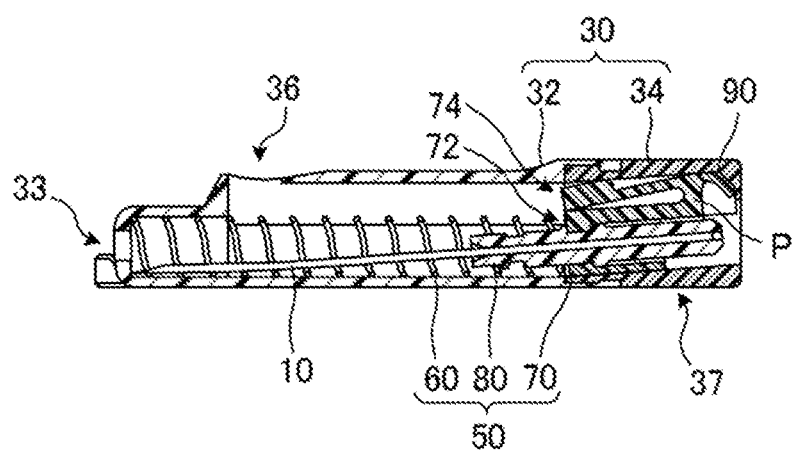
FIG. 3 is a sectional view of the medical needle in a state that a needle portion is accommodated in a case.

FIG. 1 to FIG. 3 illustrate configurations of a medical needle 1 according to embodiment 1-1 of the present invention.

The medical needle 1 is e.g. a winged needle that is used so as to be fixed while piercing a patient's skin during blood collection, blood transfusion, fluid infusion, or the like.

As illustrated in FIG. 1 to FIG. 3, the medical needle 1 according to embodiment 1-1 includes a needle portion 10 having a needle tip 14, a case 30 capable of accommodating the needle portion 10, wing portions 40 provided on a distal end portion of the case 30, a movement mechanism 50 for moving the needle portion 10 to put the needle portion 10 into the case 30, and a movement restricting portion 37 that restricts the movement of the needle portion 10 accommodated in the case 30.

In the following explanation, the position where the needle tip 14 protrudes from the case 30 by a predetermined length as illustrated in FIG. 2 is referred to as a "first position", and a position where the needle tip 14 is accommodated in the case 30 as illustrated in FIG. 3 is referred to as a "second position". The direction in which the needle portion 10 moves from the first position to the second position by the movement mechanism 50 is referred to as a "moving direction", and the direction from the second position to the first position is referred to as an "opposite direction".

Additionally, in the axial direction of the needle portion 10, the side of the needle tip 14 is referred to as a "distal end side", and the opposite side to the needle tip 14 is referred to as a "rear end side".

The needle portion 10 has a needle tube 12 composed of a hollow circular tube, and the needle tip 14 located on the distal end of the needle tube 12. The needle portion 10 is made of e.g. a metal material such as a stainless steel, aluminum, an aluminum alloy, titanium, and a titanium alloy, but may be made of a material other than the metal material, such as a resin material. A rear end portion of the needle tube 12 is connected to a tube not illustrated.

A cap not illustrated is attached to the medical needle 1 before use. For example, the cap is configured to be fittable to the distal end portion of the case 30 while covering the needle portion 10 and detachable from the distal end portion of the case 30.

As illustrated in FIG. 2 and FIG. 3, the case 30 has a cylindrical base portion 32 with opened both ends, and a cover portion 34 for closing a rear end-side opening of the base portion 32. The cover portion 34 is configured to be fittable to the rear end-side opening of the base portion 32.

Inside the base portion 32, a space is formed along a longitudinal direction of the base portion 32. The base portion 32 can accommodate the needle portion 10 in this internal space. As illustrated in FIG. 3, for example, a circular opening 33 as a hole portion through which the needle tip 14 can pass is provided on the distal end of the base portion 32. An opening diameter of the opening 33 is set to be somewhat larger than an outer diameter of the needle tube 12 such that the needle portion 10 can be exposed to the distal end side through the opening 33.

As illustrated in FIG. 3, a first engagement portion 36 is provided on a distal end-side outer face of the base portion 32. When the needle portion 10 is at the first position, the first engagement portion 36 engages with a part (a convex portion 76 of an operation portion 70) of the movement mechanism 50. The first engagement portion 36 is e.g. an angular hole communicating with the internal space of the base portion 32.

The cover portion 34 has a concave portion that is recessed toward the moving direction. A hole portion through which the tube to be connected to the needle portion 10 passes is provided on the rear end side of the cover portion 34.

The movement restricting portion 37 restricts the needle tip 14 accommodated in the case 30 from moving in the opposite direction to the moving direction of the needle portion 10. The movement restricting portion 37 according to embodiment 1-1 is arranged such that an inner face of the cover portion 34 forming the concave portion is sloped with respect to the moving direction of the needle portion 10. Thus, as illustrated in FIG. 2, an upper inner face and a lower inner face of the cover portion 34 are sloped such that their rear end sides face upward with respect to the longitudinal direction of the base portion 32. For example, the upper inner face and the lower inner face of the cover portion 34 are parallel to each other.

As illustrated in FIG. 3, once the needle portion 10 and the movement mechanism 50 move into the cover portion 34, the distal end sides of the needle portion 10 and the movement mechanism 50 incline downward with respect to the longitudinal direction of the base portion 32 along the inner face of the movement restricting portion 37. Thereby, the needle portion 10 is accommodated in the base portion 32 in a direction intersecting the moving direction. Since the needle tip 14 accommodated in the base portion 32 of the case 30 is directed not to the opening 33 but to the distal end-side inner face of the base portion 32, the needle portion 10 is maintained such that the needle tip 14 can come into contact with the inner face.

As illustrated in FIG. 1, the wing portions 40 are a pair of wing-shaped members arranged so as to be individually connected to both side faces of the distal end portion of the base portion 32. Each of the wing portions 40 has a grip portion 42 and a thin portion 44 formed thinner than a thickness of the grip portion 42. The grip portion 42 is configured to be rotatable by a predetermined degree around a connecting portion between the base portion 32 and the thin portion 44, as an axis.

As illustrated in FIG. 2 and FIG. 3, the movement mechanism 50 has the spring 60, the operation portion 70, and a fixation portion 80 for fixing the operation portion 70 to the needle portion 10, which are disposed in the internal space of the base portion 32.

The spring 60 as an elastic member is e.g. a metal coil spring and is arranged in a compressed state in the internal space of the base portion 32. A distal end-side edge of the spring 60 is in contact with the distal end-side inner face of the base portion 32. As illustrated in FIG. 2 and FIG. 3, a rear end-side edge of the spring 60 is in contact with a distal end-side face of the operation portion 70. When the needle tip 14 is at the first position, the spring 60 is compressed more strongly than when the needle tip 14 is at the second position, and when the needle tip 14 is at the second position, the spring 60 energizes the needle portion 10 fixed to the operation portion 70 toward the rear end side.

The operation portion 70 has e.g. a circular tube-shaped joint portion 72 and an operation end 74 disposed on an upper side of the joint portion 72.

The operation end 74 is a member that is a substantially U-shaped member arranged sideways on the upper position of the joint portion 72. The upper portion of the operation end 74 is formed e.g. in a lever shape (rod shape) with a rear end portion as a fulcrum. A lower portion of the operation end 74 is connected and fixed to the joint portion 72, but a distal end side of the upper portion of the operation end 74 is not fixed and is a free end.

The convex portion 76 capable of engaging with the first engagement portion 36 is provided on the distal end of the upper portion of the operation end 74. A flat shape of the convex portion 76 corresponds to the opening shape of the first engagement portion 36, and is e.g. a substantially quadrangle shape. For example, the upper portion of the operation end 74 has such an elasticity that warps the upper portion downward when receiving a force from the upper side, and the posture of the upper portion is maintained so as to be energized upward when receiving no force from the upper side, to maintain the engaged state with the first engagement portion 36.

The fixation portion 80 is e.g. a circular tube-shaped member, through which the needle portion 10 can pass. A tube outer diameter of the fixation portion 80 is set to such a dimension that the fixation portion 80 can be inserted into the joint portion 72.

The fixation portion 80 and the operation portion 70 are configured to be fittable to each other. For example, they are configured such that two flange portions are provided in combination on an outer peripheral face of the fixation portion 80, the distal end-side inner diameter of the joint portion 72 is made smaller than those of the other portions, and the joint portion 72 can be fitted to between the two flange portions of the fixation portion 80. In addition, a groove is provided on an inner face of the joint portion 72, and a projection fittable to the groove is provided on the outer face of the fixation portion 80.

A curved portion 90 is provided on a part of the movement mechanism 50. The curved portion 90 according to embodiment 1-1 is connected to a rear end side (opposite side to the position of the convex portion 76) of the upper portion of the operation end 74. The curved portion 90 is curved e.g. in a banana shape so as to hang down from the upper position of the operation end 74. The curved portion 90 is configured to be further curved and warped once receiving a load in a predetermined degree or higher.

An inner face shape of the cover portion 34 opposed to the curved portion 90 is a curved shape as illustrated in FIG. 2. The curved shape of the cover portion 34 is configured such that the cover portion 34 is in contact with and fit to the curved face of the curved portion 90 when the needle portion 10 is at the second position.

The base portion 32, the cover portion 34, the wing portions 40, the operation portion 70, the fixation portion 80, and the curved portion 90 are made of e.g. a plastic material such as polycarbonate and polypropylene. The base portion 32 and the wing portions 40, as well as the operation portion 70 and the curved portion 90 are integrally molded as one component respectively e.g. by injection molding. The cover portion 34 is molded independently from the base portion 32 and then pressed into the rear end-side opening of the base portion 32 and fit-fixed, but may be adhesively fixed with an adhesive.

The needle portion 10 and the fixation portion 80 are connected and fixed to each other e.g. by using an adhesive in a state that the needle portion 10 passes through the fixation portion 80. In addition, the joint portion 72 of the operation portion 70 is inserted through and fixed to the fixation portion 80. Since the joint portion 72 and the fixation portion 80 are fitted to each other, their positions can be fixed in a state that their longitudinal direction-positions and rotational direction-positions are matched.

Although the spring 60 is disposed on the outer peripheral face of the fixation portion 80, the spring 60 does not come into contact with the needle portion 10 and the fixation portion 80 but with the operation portion 70. For example, the spring 60 may be adhesively fixed to the distal end-side face of the operation portion 70, or may be mounted without adhesion or the like.

Next, a method for using the medical needle 1 will be explained.

First, the cap is removed from the medical needle 1 in a state that the needle tip 14 is at the first position, to expose the needle tip 14. Then, while gripping the grip portions 42 of the wing portions 40, the needle tip 14 is stuck into the patient's skin. After the sticking, as necessary, the grip portion 42 is widened, and taping is conducted from above the grip portion 42.

When drawing the needle tip 14 out from the patient's skin, the convex portion 76 of the operation portion 70 is pressed downward to release the engagement between the operation portion 70 (convex portion 76) and the first engagement portion 36. Once the engagement is released, the movement mechanism 50 moves together with the needle portion 10 from the first position to the second position by the action of the spring 60, and the needle tip 14 is drawn out from the patient's skin. At this time, the action of the curved portion 90 reduces impact due to the contact between the curved portion 90 and the cover portion 34 and also suppresses occurrence of a collision noise. When drawing the needle tip 14 out from the patient's skin, a process may be executed, in which the needle tip 14 is first drawn out from the patient's skin, then the convex portion 76 of the operation portion 70 is pressed downward to put the needle portion 10 into the case 30.

Once the needle portion 10 and the movement mechanism 50 move to the second position, the distal end sides of the needle portion 10 and the movement mechanism 50 incline downward with respect to the longitudinal direction of the base portion 32 along the inner face of the movement restricting portion 37. Thus, the posture of the needle portion 10 is maintained in the direction in which an axial direction of the needle tube 12 intersects with the moving direction. Thereby, the needle tip 14 is maintained so as to be contactable with the inner face of the case 30, specifically the distal end-side inner face of the base portion 32. Even if an action of moving the needle portion 10 accommodated in the case 30 in the opposite direction is caused, the needle tip 14 comes into contact with the inner face of the case 30, and therefore the needle tip 14 can be prevented from being exposed to the outside of the case 30.

At the second position, the operation end 74 of the operation portion 70 is compressed in the cover portion 34, so that the operation end 74 acts as a leaf spring. While a connection portion P between the operation end 74 and the curved portion 90 serves as a fulcrum, a downward reaction force is effected from the operation end 74 to the needle portion 10 and the movement mechanism 50, so that the needle portion 10 and the movement mechanism 50 are pressed toward the lower inner face of the cover portion 34. Thereby, the posture of the inclined needle portion 10 can be easily maintained, and it is easier to prevent the needle tip 14 from moving in the opposite direction.

In addition, when the curved portion 90 located on the rear end side of the operation portion 70 is warped, the needle portion 10 is pushed back to the distal end side while the distal end side of the needle portion 10 is still inclined downward. Since the needle tip 14 is pressed against the distal end-side inner face of the base portion 32, it is easier to prevent the needle tip 14 from moving in the opposite direction.

The medical needle 1 according to embodiment 1-1 configured as above includes the needle portion 10 having the needle tip 14 on the distal end, the case 30 configured to be capable of exposing the needle portion 10 to the distal end side and accommodating the needle portion 10, the movement mechanism 50 for moving the needle portion 10 inside the case 30 until the needle tip 14 protruding from the case 30 is accommodated in the case 30, and the movement restricting portion 37 that restricts the needle tip 14 accommodated in the case 30 from moving in the opposite direction to the moving direction of the needle portion 10 by the movement mechanism 50. The movement restricting portion 37 maintains the needle tip 14 accommodated in the case 30 such that the needle tip 14 can come into contact with the inner face of the case 30 to restrict the movement of the needle tip 14 in the opposite direction.

According to embodiment 1-1, the movement of the needle tip 14 accommodated in the case 30 toward the outside of the case 30 is restricted by the movement restricting portion 37, and the needle tip 14 can be maintained in the case 30. Thus, the needle tip 14 can be prevented from protruding to the outside of the case 30 again to cause erroneous sticking.

The present invention is not limited to the examples described in the aforementioned embodiment, and can be implemented in various aspects without departing from the gist of the present invention. For example, the following modifications are also possible.

Modification Example

In the medical needle 1, a part of at least either the movement mechanism 50 or the needle portion 10 may be engaged with the engaged part of the cover portion 34 to restrict the movement of the needle tip 14 in the opposite direction.

Figure 4:
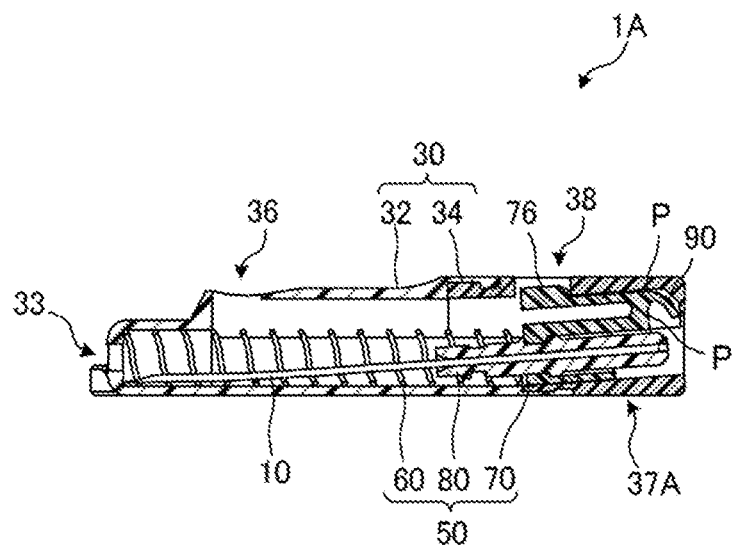
FIG. 4 is a sectional view of the medical needle in which a movement mechanism and a cover portion can engage with each other.

FIG. 4 is a sectional view of a medical needle 1A in a case where a movement mechanism 50 engages with the cover portion 34.

In the medical needle 1A, a second engagement portion 38 is provided as the engaged part on the inner face of the cover portion 34. When the needle portion 10 is at the second position, the second engagement portion 38 engages with the convex portion 76 of the operation portion 70 as a part of the movement mechanism 50. The second engagement portion 38 is an angular hole communicating with the internal space of the cover portion 34.

The shape of the second engagement portion 38 is not limited to the angular hole as long as the second engagement portion 38 can engage with a part of the movement mechanism 50. For example, the second engagement portion 38 may be a different level face provided on the inner face of the cover portion 34. A level of the inner face of the cover portion 34 on the rear end side of the different level face is set to be higher than a level of the inner face of the cover portion 34 on the distal end side of the different level face. Since the distal end-side face of the convex portion 76 of the operation portion 70 comes into contact with the different level face, the operation portion 70 and the second engagement portion 38 engage with each other.

When the needle portion 10 is accommodated in the case 30, the movement restricting portion 37A not only maintains the needle tip 14 so as to be contactable with the inner face of the case 30 but also engages the convex portion 76 of the operation portion 70 with the second engagement portion 38 to restrict the movement of the operation portion 70. Thereby, the operation portion 70 and accordingly the needle portion 10 can be firmly fixed at the second position to maintain the needle tip 14 in the case 30.

In the medical needle 1A, when the curved portion 90 comes into contact with the cover portion 34 and is warped, the convex portion 76 located on the opposite side to the curved portion 90 is displaced upward while the connection portion P between the curved portion 90 and the operation end 74 serves as a fulcrum, so that the operation end 74 is pressed against the inner face of the base portion 32. The convex portion 76 further make inroads into the second engagement portion 38, and the convex portion 76 and the second engagement portion 38 more firmly engage with each other. The operation portion 70 and accordingly the needle portion 10 can be more firmly fixed at the second position.

Figure 5:
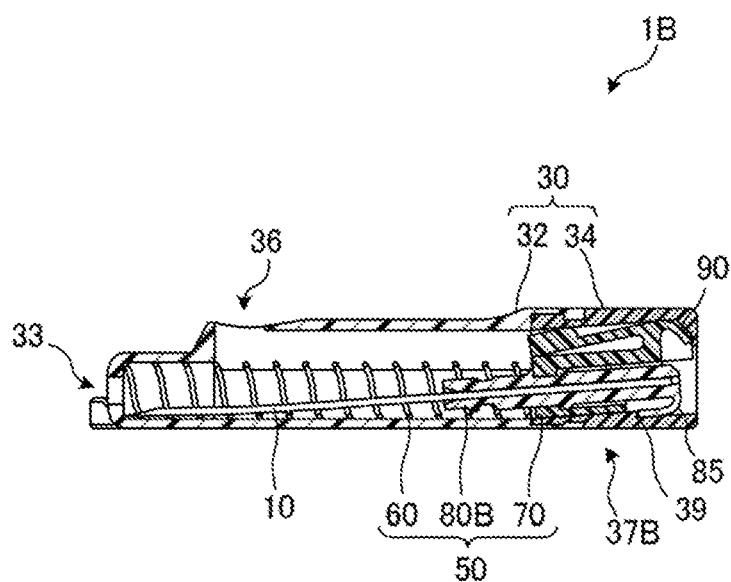
FIG. 5 is a sectional view of the medical needle in which the needle portion and the cover portion can engage with each other.

FIG. 5 is a sectional view illustrating a medical needle 1B in a case where the needle portion 10 engages with the cover portion 34.

In the medical needle 1B, similarly to the movement restricting portion 37, a movement restricting portion 37B is arranged such that the inner face of the cover portion 34 forming the concave portion is sloped with respect to the moving direction of the needle portion 10.

In addition, a third engagement portion 39 as an engaged part that engages with a part of the needle portion 10 is provided on the inner face of the concave portion of the cover portion 34. In the medical needle 1B, a fixation portion 80B that is a supporting member for the needle portion 10 is provided on the rear end portion of the needle portion 10, and the third engagement portion 39 engages with a part of the fixation portion 80B. The third engagement portion 39 is a different level face provided on the inner face of the cover portion 34. The level of the inner face of the cover portion 34 on the distal end side of the different level face is set to be higher than the level of the inner face of the cover portion 34 on the rear end side of the different level face.

The fixation portion 80B has an arm 85 that extends in the opposite direction to the moving direction while curving from the lower position of the rear end portion. A distal end face of the arm 85 comes into contact with the different level face of the third engagement portion 39, so that the fixation portion 80B and the third engagement portion 39 engage with each other. For example, the arm 85 has such an elasticity that the arm 85 is warped upward once a force is applied from the lower side. In addition, the arm 85 is configured such that, when no force is applied from the lower side, the arm 85 is energized downward to maintain the engaged state with the third engagement portion 39.

When the needle portion 10 is accommodated in the case 30, the movement restricting portion 37B not only maintains the needle tip 14 so as to be contactable with the inner face of the case 30 but also engages the distal end of the arm 85 with the third engagement portion 39 to restrict the movement of the needle portion 10 in the opposite direction. Thereby, the needle portion 10 can be firmly fixed at the second position to maintain the needle tip 14 in the case 30.

In the medical needle 1B, the third engagement portion 39 is provided on the inner face of the cover portion 34 where the user cannot directly touch with hands. Accidental release of the engagement can be prevented, and the needle tip 14 can be easily maintained in the case 30.

Embodiment 1-2

Figure 6:
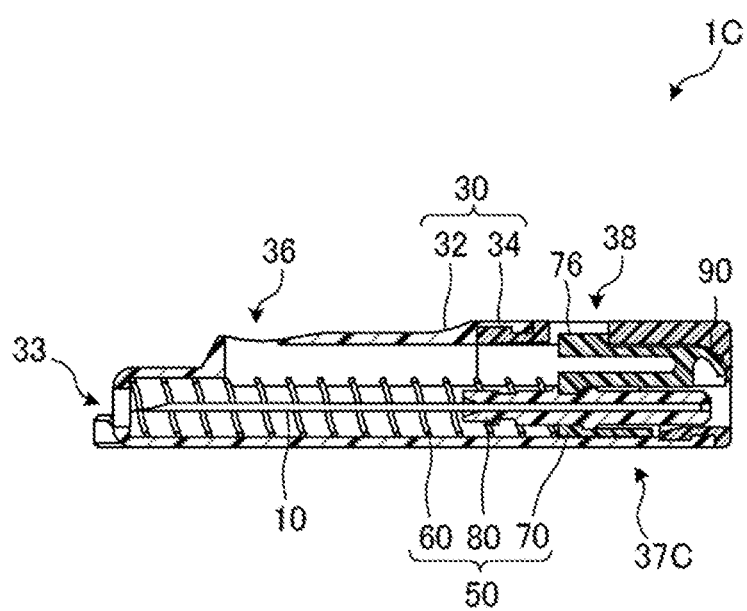
FIG. 6 is a sectional view of a medical needle according to embodiment 1-2.

FIG. 6 is a sectional view illustrating a medical needle 1C according to embodiment 1-2. In the medical needle 1C according to embodiment 1-2, the movement restricting portion restricts the movement of the needle tip 14 in the opposite direction only by engagement. Note that configurations other than configurations to be explained in detail below are the same as in embodiment 1-1, and detailed explanation of the same configurations is omitted.

In the medical needle 1C, the second engagement portion 38 is provided on the inner face of the concave portion of the cover portion 34, but the inner face of the cover portion 34 is not sloped, and is parallel to the moving direction of the needle portion 10. When the needle portion 10 is accommodated in the case 30, a movement restricting portion 37C of the medical needle 1C restricts the movement of the needle tip 14 in the opposite direction by engaging the convex portion 76 of the movement mechanism 50 with the second engagement portion 38.

The medical needle 1C according to embodiment 1-2 configured as above includes the needle portion 10 having the needle tip 14 on the distal end, the case 30 configured to be capable of exposing the needle portion 10 to the distal end side and accommodating the needle portion 10, the movement mechanism 50 for moving the needle portion 10 inside the case 30 until the needle tip 14 protruding from the case 30 is accommodated in the case 30, and the movement restricting portion 37C that restricts the needle tip 14 accommodated in the case 30 from moving in the opposite direction to the moving direction of the needle portion 10 by the movement mechanism 50. The movement restricting portion 37C engages a part (convex portion 76) of the movement mechanism 50 with the engaged part (second engagement portion 38) of the cover portion 34 to restrict the movement of the needle tip 14 in the opposite direction.

According to embodiment 1-2, the movement of the needle tip 14 accommodated in the case 30 toward the outside of the case 30 is restricted by the movement restricting portion 37C, and the needle tip 14 can be maintained in the case 30. Thus, the needle tip 14 can be prevented from protruding to the outside of the case 30 again to cause erroneous sticking.

Although the case where the base portion 32 and the cover portion 34 in the case 30 are separately molded has been described as an example in the aforementioned embodiments and modification example, the present invention is not limited to this configuration, and the base portion and the cover portion may be integrally molded.

In addition, although the case where the coil spring is used as the spring 60 of the movement mechanism 50 and the coil spring is disposed on the distal end side of the operation portion 70 has been described as an example, the present invention is not limited to this configuration as long as an energization force for the movement can be applied by an elastic member. For example, a tensile spring may be disposed on the rear end side of the operation portion. In addition, instead of the spring, an elastic member such as a rubber may be used.

Although the winged needle that is used so as to be fixed while piercing the patient's skin has been described as an example, the present invention is not limited to this winged needle. For example, the present invention can also be applied to an indwelling needle or the like used for sustained intravenous drip infusion.

Hereinafter, embodiments of the medical needle for achieving the second object will be explained with reference to the figures.

Embodiment 2-1

FIG. 7 to FIG. 11 illustrate configurations of a medical needle 1001 according to embodiment 2-1 of the present invention.

The medical needle 1001 is e.g. a winged needle that is used so as to be fixed while piercing a patient's skin during blood collection, blood transfusion, fluid infusion, or the like.

As illustrated in FIG. 7 to FIG. 11, the medical needle 1001 according to embodiment 2-1 includes a needle portion 1010 having a needle tip 1014, a case 1030 capable of accommodating the needle portion 1010, wing portions 1040 provided on the case 1030, and a movement mechanism 1050 for moving the needle portion 1010 to put the needle portion 1010 into the case 1030.

Figure 8:
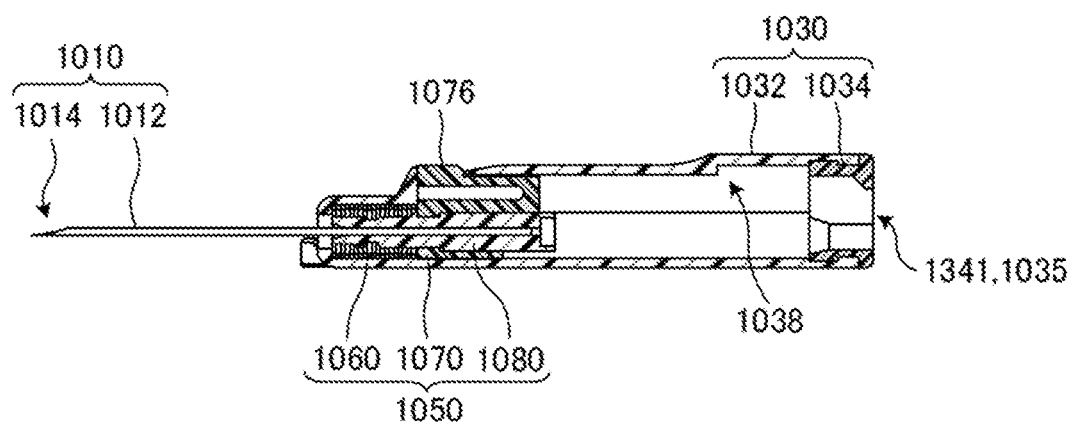
FIG. 8 is a sectional view taken along line Ia-Ia in FIG. 7.
Figure 9:
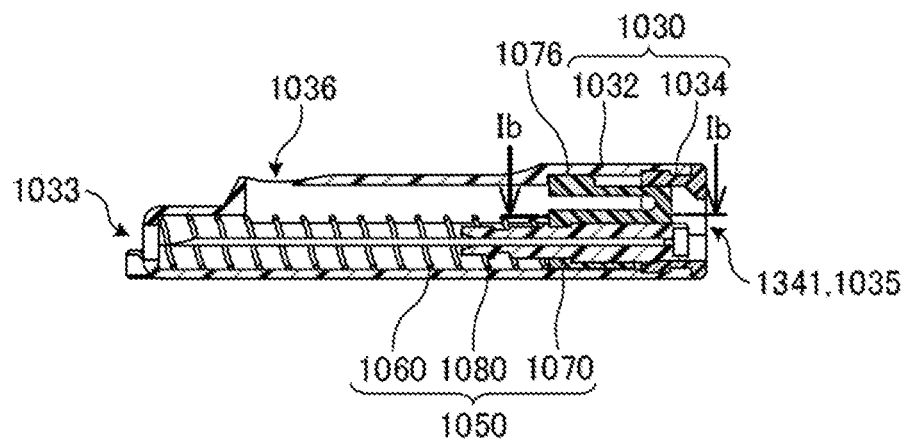
FIG. 9 is a sectional view of the medical needle in a state that a needle portion is accommodated.

In the following explanation, the position where the needle tip 1014 protrudes from the case 1030 by a predetermined length as illustrated in FIG. 8 is referred to as a "first position", and a position where the needle tip 1014 is accommodated in the case 1030 as illustrated in FIG. 9 is referred to as a "second position". A direction in which the needle portion 1010 moves from the first position to the second position by the movement mechanism 1050 is referred to as "moving direction".

Additionally, a portion toward the needle tip 1014 in the axial direction of the needle portion 1010 is referred to as a "distal end side", and an opposite portion to the needle tip 1014 is referred to as a "rear end side".

The needle portion 1010 has a needle tube 1012 composed of a hollow circular tube, and a needle tip 1014 located on the distal end of the needle tube 1012.

The needle portion 1010 is made of e.g. a metal material such as a stainless steel, aluminum, an aluminum alloy, titanium, and a titanium alloy, but may be made of a material other than the metal material, such as a resin material. A rear end portion of the needle tube 1012 is connected to a tube not illustrated.

A cap not illustrated is attached to the medical needle 1001 before use. For example, the cap can be configured to be fittable to the distal end portion of the case 1030 while covering the needle portion 1010 and to be detachable from the distal end portion of the case 1030.

As illustrated in FIG. 8 and FIG. 9, the case 1030 has a cylindrical base portion 1032 with opened both ends, and a cover portion 1034 for closing a rear end-side opening of the base portion 1032. The cover portion 1034 is configured to be fittable to the rear end-side opening of the base portion 1032.

Inside the base portion 1032, a space is formed along a longitudinal direction of the base portion 1032. The base portion 1032 can accommodate the needle portion 1010 in this internal space. As illustrated in FIG. 9, for example, a circular opening 1033 as a hole portion through which the needle tip 1014 can pass is provided on a distal end side of the base portion 1032. An opening diameter of the opening 1033 is set to be somewhat larger than an outer diameter of the needle tube 1012 such that the needle portion 1010 can be exposed to the distal end side through the opening 1033.

As illustrated in FIG. 9, a first engagement portion 1036 is provided on a distal end-side outer face of the base portion 1032. When the needle portion 1010 is at the first position, the first engagement portion 1036 engages with a part (a convex portion 1076 of an operation portion 1070) of the movement mechanism 1050. The first engagement portion 1036 is e.g. an angular hole communicating with the internal space of the base portion 1032.

A second engagement portion 1038 engaging with a part (the convex portion 1076 of the operation portion 1070) of the movement mechanism 1050 when the needle portion 1010 is at the second position is provided on a rear end-side inner face of the base portion 1032. The second engagement portion 1038 is e.g. a different level face provided on the inner face of the base portion 1032. A level of the inner face of the base portion 1032 on the rear end side of the different level face is set to be higher than a level of the inner face of the base portion 1032 on the distal end side of the different level face.

The cover portion 1034 has a concave portion 1341 that is recessed toward the moving direction for receiving the end portion of the movement mechanism 1050 that has moved to the second position. A hole portion through which the tube to be connected to the needle portion 1010 passes is provided on the rear end side of the cover portion 1034. On the cover portion 1034 according to embodiment 2-1, the rear end side of the movement mechanism 1050 is opened, but the rear end side may be closed.

Figure 11:
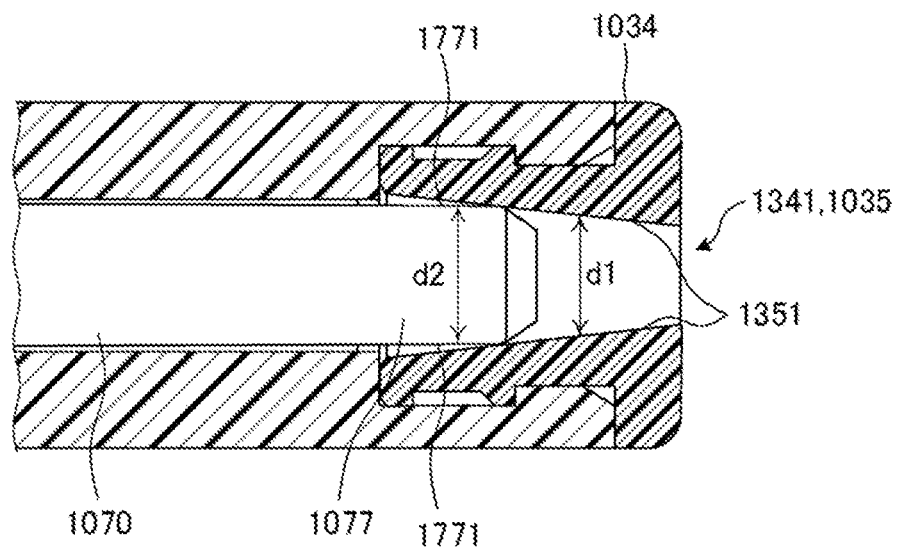
FIG. 11 is a sectional view taken along line Ib-Ib in FIG. 9.

As illustrated in FIG. 11, the concave portion 1341 functionally serves as a fitting portion 1035 that is fitted to the rear end portion of the movement mechanism 1050 that has moved to the second position. In embodiment 2-1, the operation portion 1070 is provided on the rear end portion of the movement mechanism 1050, and the fitting portion 1035 is fitted to a rear end-side portion 1077 of the operation portion 1070.

The fitting portion 1035 has a fitting face 1351 that is sloped such that an inner diameter d1 gradually decreases in the moving direction of the movement mechanism 1050. The fitting face 1351 is an inner face of the cover portion 1034 that forms the concave portion 1341. As illustrated in FIG. 11, the fitting portion 1035 has a tapered shape that the countering fitting faces 1351 are sloped in the moving direction. Once the movement mechanism 1050 moves to the second position, the fitting face 1351 comes into contact with an outer peripheral face 1771 of the rear end-side portion 1077 of the operation portion 1070 that has entered the concave portion 1341 of the cover portion 1034.

The inner diameter d1 of the fitting portion 1035 is a length between the fitting faces 1351 countering in a direction orthogonal to the moving direction. The distal end-side inner diameter d1 of the fitting portion 1035 is set to be larger than an outer diameter d2 of the rear end-side portion 1077 of the operation portion 1070 such that the rear end-side portion 1077 can be received in the concave portion 1341. The rear end-side inner diameter d1 of the fitting portion 1035 is set to be smaller than the outer diameter d2 of the rear end-side portion 1077 such that the movement of the rear end-side portion 1077 and accordingly the movement mechanism 1050 toward the rear end side can be restricted.

Figure 7:
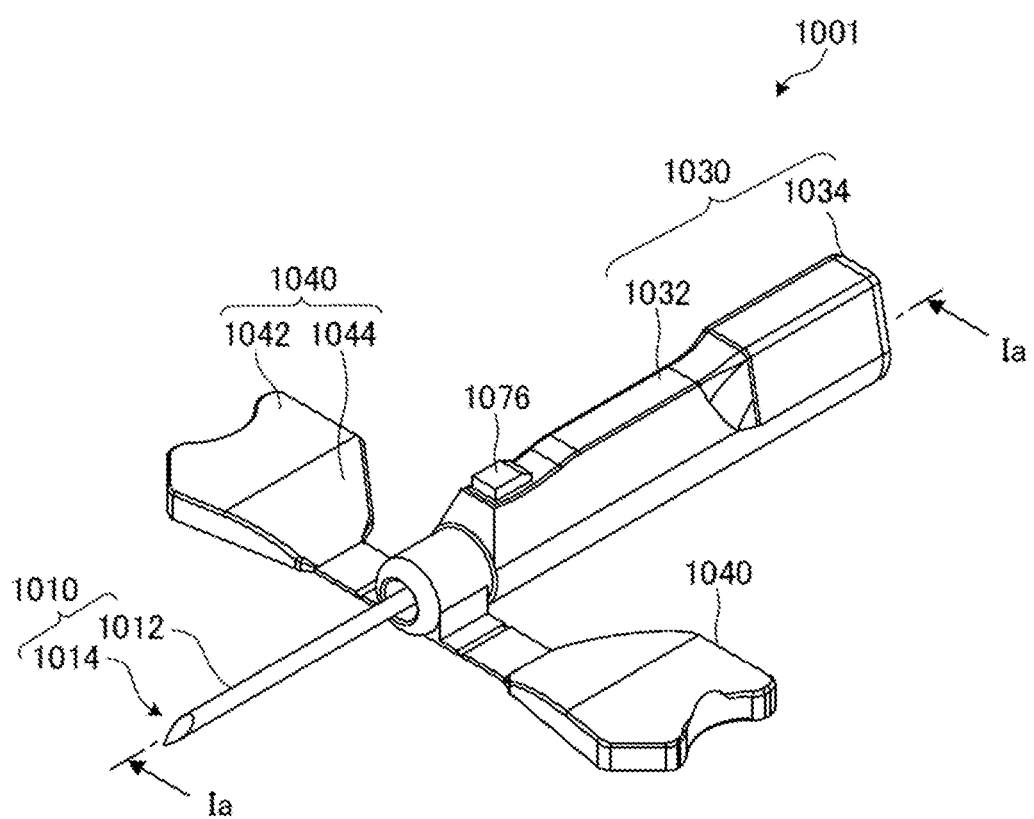
FIG. 7 is an overall perspective view of a medical needle according to embodiment 2-1.

As illustrated in FIG. 7, the wing portions 1040 are a pair of wing-shaped members arranged so as to be individually connected to both side faces of the distal end portion of the base portion 1032. Each of the wing portions 1040 has a grip portion 1042 and a thin portion 1044 formed thinner than a thickness of the grip portion 1042. The grip portion 1042 is configured to be rotatable by a predetermined degree around a connecting portion between the base portion 1032 and the thin portion 1044, as an axis.

As illustrated in FIG. 8 and FIG. 9, the movement mechanism 1050 has a spring 1060, the operation portion 1070, and a fixation portion 1080 for fixing the operation portion 1070 to the needle portion 1010, which are disposed in the internal space of the base portion 1032.

The spring 1060 as an elastic member is e.g. a metal coil spring and is arranged in a compressed state in the internal space of the base portion 1032. A distal end-side edge of the spring 1060 is in contact with the distal end-side inner face of the base portion 1032. As illustrated in FIG. 8 and FIG. 9, a rear end-side edge of the spring 1060 is in contact with a distal end-side face of the operation portion 1070. When the needle tip 1014 is at the first position, the spring 1060 is compressed more strongly than when the needle tip 1014 is at the second position, and when the needle tip 1014 is at the second position, the spring 1060 energizes the needle portion 1010 fixed to the operation portion 1070 toward the rear end side.

Figure 10:
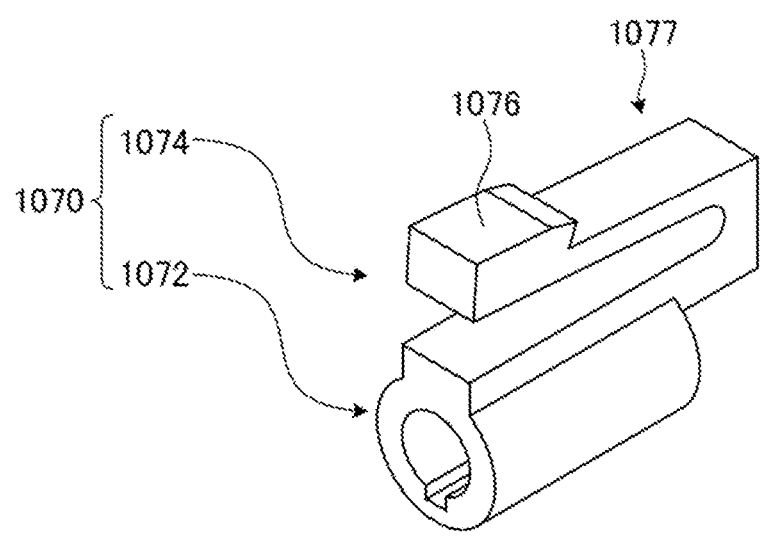
FIG. 10 is a perspective view illustrating an operation portion.

As illustrated in FIG. 10, the operation portion 1070 has e.g. a circular tube-shaped joint portion 1072 and an operation end 1074 disposed on an upper side of the joint portion 1072. The operation end 1074 is a member that a substantially U-shaped member is arranged sideways on the upper position of the joint portion 1072. The upper portion of the operation end 1074 is formed e.g. in a lever shape (rod shape) with a rear end portion as a fulcrum. A lower portion of the operation end 1074 is connected and fixed to the joint portion 1072, but a distal end side of the upper portion of the operation end 1074 is not fixed and is a free end.

The convex portion 1076 capable of engaging with the first engagement portion 1036 and the second engagement portion 1038 is provided on the distal end of the upper portion of the operation end 1074. A flat shape of the convex portion 1076 corresponds to the opening shape of the first engagement portion 1036, and is e.g. a substantially quadrangle shape. For example, the upper portion of the operation end 1074 has such an elasticity that warps the upper portion downward when receiving a force from the upper side, and is energized upward when receiving no force from the upper side, and the posture of the upper portion is maintained so as to maintain the engaged state with the first engagement portion 1036.

The fixation portion 1080 is e.g. a circular tube-shaped member, through which the needle portion 1010 can pass. A tube outer diameter of the fixation portion 1080 is set to such a dimension that the fixation portion 1080 can be inserted into the joint portion 1072.

The fixation portion 1080 and the operation portion 1070 are configured to be fittable to each other. For example, the fixation portion 1080 and the operation portion 1070 are configured such that two flange portions are provided in combination on an outer peripheral face of the fixation portion 1080, and the distal end-side inner diameter of the joint portion 1072 is made smaller than those of the other portions so that the joint portion 1072 can be fitted to between the two flange portions of the fixation portion 1080. In addition, a groove is provided on an inner face of the joint portion 1072, and a projection fittable to the groove is provided on the outer face of the fixation portion 1080.

The base portion 1032, the cover portion 1034, the wing portions 1040, the operation portion 1070, and the fixation portion 1080 are made of e.g. a plastic material such as polycarbonate and polypropylene. The base portion 1032 and the wing portions 1040 are integrally molded as one member by e.g. injection molding. The cover portion 1034 is molded independently from the base portion 1032 and then pressed into the rear end-side opening of the base portion 1032 and fit-fixed, but may be adhesively fixed with an adhesive.

Since the cover portion 1034 that functionally serves as the fitting portion 1035 reduces impact due to the contact during the fitting, the cover portion 1034 may be made of a flexible material such as a resin, a silicone, and a rubber, by rubber molding or resin injection molding, or the like.

The needle portion 1010 and the fixation portion 1080 are connected and fixed to each other e.g. by using an adhesive in a state that the needle portion 1010 passes through the fixation portion 1080. In addition, the joint portion 1072 of the operation portion 1070 is inserted through and fixed to the fixation portion 1080. Since the joint portion 1072 and the fixation portion 1080 are fitted to each other, their positions can be fixed in a state that their longitudinal direction-positions and rotational direction-positions are matched.

Although the spring 1060 is disposed on the outer peripheral face of the fixation portion 1080, the spring 1060 does not come into contact with the needle portion 1010 or the fixation portion 1080, but with the operation portion 1070. For example, the spring 1060 may be adhesively fixed to the distal end-side face of the operation portion 1070, or may be mounted without adhesion or the like.

Next, a method for using the medical needle 1001 will be explained.

First, the cap is removed from the medical needle 1001 in a state that the needle tip 1014 is at the first position, to expose the needle tip 1014. Then, while gripping the grip portions 1042 of the wing portions 1040, the needle tip 1014 is stuck into a patient's skin. After the sticking, as necessary, the grip portions 1042 are widened, and taping is conducted from above the grip portions 1042.

When drawing the needle tip 1014 out from the patient's skin, the convex portion 1076 of the operation portion 1070 is pressed downward to release the engagement between the operation portion 1070 (convex portion 1076) and the first engagement portion 1036. Once the engagement is released, the movement mechanism 1050 moves together with the needle portion 1010 from the first position to the second position by the action of the spring 1060, and the needle tip 1014 is drawn out from the patient's skin. When drawing the needle tip 1014 out from the patient's skin, a process may be executed, in which the needle tip 1014 is first drawn out from the patient's skin, then the convex portion 1076 of the operation portion 1070 is pressed downward to put the needle portion 1010 into the case 1030.

Once the operation portion 1070 enters the concave portion 1341 of the cover portion 1034 by the movement to the second position, the outer peripheral face 1771 of the rear end-side portion 1077 comes into contact with the fitting face 1351 of the fitting portion 1035.

Specifically, as a result, the repulsive force of the spring 1060 pushes the rear end-side portion 1077 into the concave portion 1341, and the more forward the rear end-side portion 1077 that has entered the concave portion 1341 moves in the moving direction, the larger the contact area between the outer peripheral face 1771 of the rear end-side portion 1077 and the fitting face 1351 is. Also, for example, if an accuracy of assembly among the components is low, or if a dimensional error is large, the more forward the rear end-side portion 1077 moves in the moving direction, the larger the contact area between the outer peripheral face 1771 of the rear end-side portion 1077 and the fitting face 1351 is. Thereby, friction between the outer peripheral face 1771 and the fitting face 1351 becomes large, and the moving speed of the movement mechanism 1050 gradually decreases.

Then, the rear end-side portion 1077 is fitted to the fitting portion 1035 at a position where the inner diameter d1 of the fitting portion 1035 and the outer diameter d2 of the rear end-side portion 1077 are equal. The fitting stops the movement mechanism 1050, and the movement of the movement mechanism 1050 toward the rear end side is restricted.

As described above, the medical needle 1001 according to embodiment 2-1 includes the needle portion 1010 having the needle tip 1014 on the distal end, the case 1030 configured to be capable of exposing the needle portion 1010 from the distal end side and accommodating the needle portion 1010, and the movement mechanism 1050 for moving the needle portion 1010 inside the case 1030 until the needle tip 1014 protruding from the case 1030 is accommodated in the case 1030. The case 1030 has a base portion 1032 having a hole portion (opening 1033) through which the needle tip 1014 can pass and a cover portion 1034 for closing the opening on the opposite side to the hole portion of the base portion 1032. The cover portion 1034 has the fitting portion 1035 that is fitted to the end portion (operation portion 1070) of the movement mechanism 1050 when the needle portion 1010 is moved, and the fitting portion 1035 has the fitting face 1351 that is sloped so as to gradually decrease in diameter in the moving direction of the needle portion 1010.

According to embodiment 2-1, when the needle portion 1010 is moved toward the second position, friction between the sloped fitting face 1351 and the movement mechanism 1050 can be gradually increased. Since the moving speed of the movement mechanism 1050 can be reduced until the movement mechanism 1050 is fitted to the fitting portion 1035, impact and noise caused when the needle portion 1010 is accommodated in the case 1030 can be suppressed even if the spring 1060 having a relatively strong repulsive force is used as an elastic member. That means, the medical needle 1001 according to the embodiment 2-1 can alleviate a discomfort feeling of the user while securely accommodating the needle tip 1014 in the case 1030.

Since the fitting face 1351 of the fitting portion 1035 comes into contact with not the whole face of the outer peripheral face 1771 of the movement mechanism 1050 but a part of the rear end side of the outer peripheral face 1771, the impact and noise due to the contact can be further reduced compared to a case where the whole faces of the members are allowed to momentarily collide with each other.

In addition, since the rear end-side portion 1077 of the operation portion 1070 for moving the needle portion 1010 is fitted to the fitting portion 1035, addition of members or change to a complicated structure are not required. With a simpler structure, an effect of suppressing impact and noise can be exhibited, and costs can be reduced.

On the other hand, at the second position, the convex portion 1076 of the operation portion 1070 engages with the second engagement portion 1038, so that the movement of the operation portion 1070 toward the distal end side is restricted. As described above, since the movement of the operation portion 1070 toward the rear end side is restricted by the fitting with the fitting portion 1035, the operation portion 1070 and accordingly the needle portion 1010 can be firmly fixed at the second position.

The present invention is not limited to the examples illustrated in embodiment 2-1 described above, and can be implemented in various aspects without departing from the gist of the present invention. The following modifications are also possible.

Modification Example

In embodiment 2-1 described above, the fitting face 1351 of the fitting portion 1035 is sloped, but the outer peripheral face 1771 of the rear end-side portion 1077 of the operation portion 1070 may be sloped.

Figure 12:
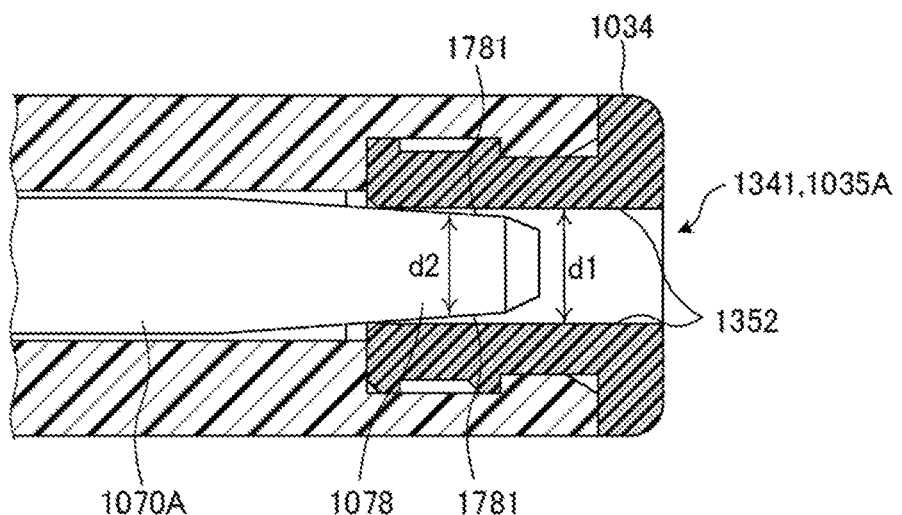
FIG. 12 is a sectional view illustrating an example that an outer peripheral face of the operation portion is sloped.

FIG. 12 is a sectional view illustrating an operation portion 1070A having a sloped outer peripheral face 1781.

As illustrated in FIG. 12, a fitting face 1352 of a fitting portion 1035A is parallel to the moving direction of the movement mechanism 1050. On the other hand, the outer peripheral face 1781 of a rear end-side portion 1078 of the operation portion 1070A is sloped such that an outer diameter d2 gradually decreases in the moving direction. A rear end-side outer diameter d2 of the rear end-side portion 1078 is set to be smaller than an inner diameter d1 of the fitting portion 1035A such that the rear end-side portion 1078 can enter the concave portion 1341 of the cover portion 1034. The distal end-side outer diameter d2 of the rear end-side portion 1078 is set to be larger than the inner diameter d2 of the fitting portion 1035A such that the movement of the rear end-side portion 1078 and accordingly the movement mechanism 1050 toward the rear end side can be restricted.

When the needle portion 1010 moves to the second position, the more forward the needle portion 1010 advances, the larger the contact area between the outer peripheral face 1781 of the operation portion 1070A and the fitting face 1352 of the fitting portion 1035A is. Since the friction gradually increases, the moving speed of the movement mechanism 1050 gradually decreases. Thus, as in embodiment 2-1 described above, it is possible to reduce the impact caused by the contact between the case 1030 and the movement mechanism 1050 to suppress occurrence of the collision noise.

Then, the rear end-side portion 1078 is fitted to the fitting portion 1035A at a position where the outer diameter d2 of the operation portion 1070A and the inner diameter d1 of the fitting portion 1035A are equal. The fitting stops the movement mechanism 1050, and the movement of the movement mechanism 1050 toward the rear end side is restricted.

As described above, if either the end portion of the movement mechanism 1050 or the fitting portion 1035 has a fitting face that is sloped so as to gradually decrease in the diameter in the moving direction of the movement mechanism 1050, the impact and noise caused when the needle tip 1014 is accommodated in the case 1030 can be reduced to alleviate the user's discomfort feeling.

Embodiment 2-2

In the medical needle according to embodiment 2-2, a fitting portion that is fitted to the end portion of the needle portion 1010 is provided on the cover portion 1034.

That means, the cover portion 1034 may have the fitting portion that is fitted to the end portion of the needle portion 1010 instead of the movement mechanism 1050.

Note that configurations other than configurations to be explained in detail below are the same as in embodiment 2-1, and detailed explanation of the same configurations is omitted.

Figure 13:
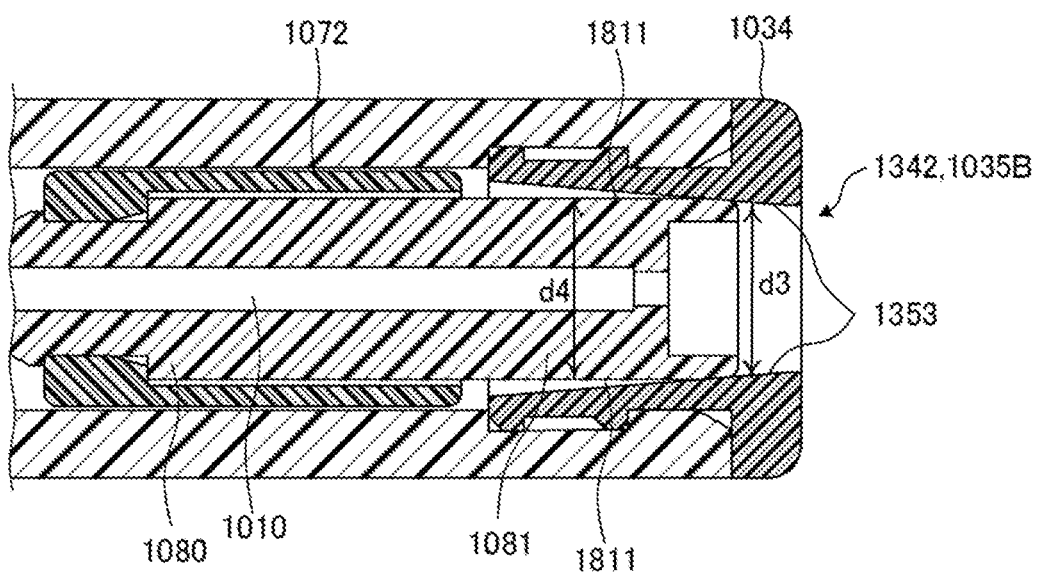
FIG. 13 is a sectional view illustrating an example of a fitting portion that is fitted to the needle portion in the medical needle of embodiment 2-2.

FIG. 13 is a sectional view illustrating a fitting portion 1035B that is fitted to the needle portion 1010. This sectional view is viewed from above the section taken along the central axis of the needle tube 1012.

As illustrated in FIG. 13, the cover portion 1034 has a concave portion 1342 recessed in the moving direction for receiving the needle portion 1010 that has moved to the second position. The concave portion 1342 functionally serves as the fitting portion 1035B that is fitted to the rear end portion of the needle portion 1010. In embodiment 2-2, the fixation portion 1080 that is a supporting member for the needle portion 1010 is provided on the rear end portion of the needle portion 1010, and the fitting portion 1035B is fitted to a rear end-side portion 1081 of the fixation portion 1080.

The fitting portion 1035B has a fitting face 1353 that is sloped such that an inner diameter d3 gradually decreases in the moving direction. The fitting face 1353 is an inner face of the cover portion 1034 that forms the concave portion 1342. Once the needle portion 1010 moves to the second position, the fitting face 1353 comes into contact with an outer peripheral face 1811 of the rear end-side portion 1081 of the fixation portion 1080 that has entered the concave portion 1342.

The inner diameter d3 of the fitting portion 1035B is a length between the fitting faces 1353 facing each other in a direction orthogonal to the moving direction. The distal end-side inner diameter d3 of the fitting portion 1035B is set to be larger than an outer diameter d4 of the rear end-side portion 1081 of the fixation portion 1080 such that the rear end-side portion 1081 can be received in the concave portion 1342. The rear end-side inner diameter d3 of the fitting portion 1035B is set to be smaller than the outer diameter d4 of the rear end-side portion 1081 such that the movement of the rear end-side portion 1081 and accordingly the needle portion 1010 toward the rear end side is restricted. The outer diameter d4 is the diameter of the circular tube-shaped fixation portion 1080.

Once the needle portion 1010 moves to the second position and the fixation portion 1080 enters the concave portion 1342 of the cover portion 1034, the outer peripheral face 1811 of the rear end-side portion 1081 comes into contact with the fitting face 1353 of the fitting portion 1035B. The more forward the rear end-side portion 1081 that has pushed into the concave portion 1342 by the repulsive force of the spring 1060 moves in the moving direction, the larger the contact area between the outer peripheral face 1811 of the rear end-side portion 1081 and the fitting face 1353 is. Also, for example, if an accuracy of assembly among the components is low, or if a dimensional error is large, the more forward the rear end-side portion 1081 moves in the moving direction, the larger the contact area between the outer peripheral face 1811 and the fitting face 1353 is. Thereby, friction between the outer peripheral face 1811 and the fitting face 1353 becomes large, and the moving speed of the needle portion 1010 gradually decreases. Then, the rear end-side portion 1081 is fitted to the fitting portion 1035B at a position where the inner diameter d3 of the fitting portion 1035B and the outer diameter d4 of the rear end-side portion 1081 are equal. The fitting stops the needle portion 1010, and the movement of the needle portion 1010 toward the rear end side is restricted.

As described above, in the medical needle according to embodiment 2-2, the cover portion 1034 has the fitting portion 1035B to be fitted to the end portion (fixation portion 1080) of the needle portion 1010 that has been moved by the movement mechanism 1050. The fitting portion 1035B has a fitting face 1353 that is sloped so as to gradually decrease in the diameter in the moving direction of the needle portion 1010.

Since the moving speed of the needle portion 1010 gradually decreases by the sloped fitting face 1353, the impact and noise caused when the needle tip 1014 is accommodated in the case 1030 by the action of the spring 1060 can be reduced, just as in embodiment 2-1 described above. In addition, since a part of the outer peripheral face 1811 of the rear end-side portion 1081 of the fixation portion 1080 comes into contact with the fitting face 1353, the impact and noise can be further suppressed compared to the case where the whole of the outer peripheral face 1811 momentarily comes into contact with the fitting face 1353.

Modification Example

If either the end portion of the needle portion 1010 or the fitting portion 1035B has a fitting face that is sloped so as to gradually decrease in the diameter in the moving direction of the movement mechanism 1050, the impact and noise caused when the needle tip 1014 is accommodated in the case 1030 can be reduced to alleviate the user's discomfort feeling. Thus, in embodiment 2-2, the outer peripheral face 1811 of the rear end-side portion 1081 of the fixation portion 1080 may be sloped instead of the fitting face 1353 of the fitting portion 1035B.

Figure 14:
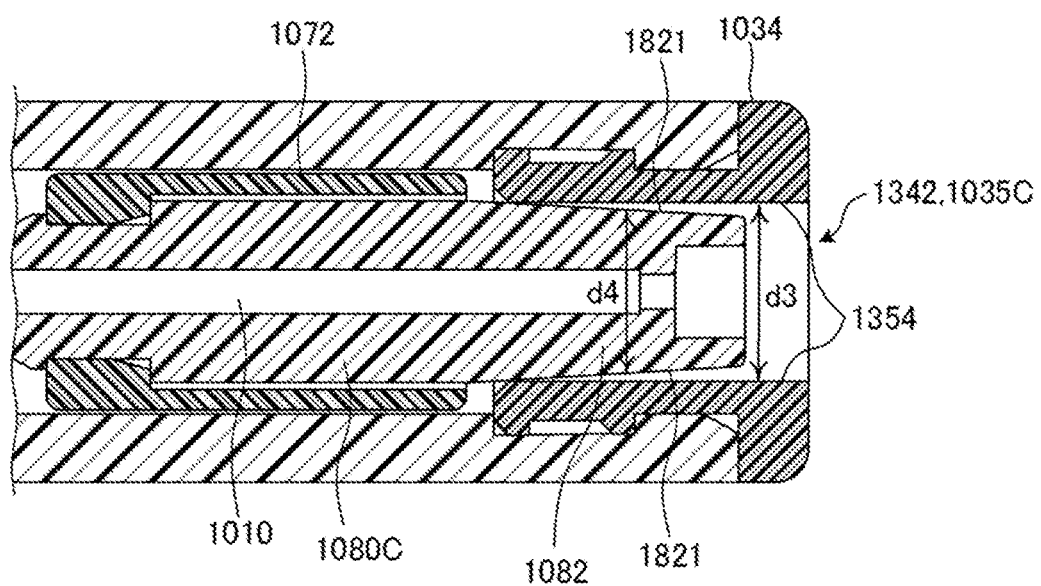
FIG. 14 is a sectional view illustrating an example that an outer peripheral face of a fixation portion for holding the needle portion is sloped.

FIG. 14 is a sectional view illustrating a fixation portion 1080C having a sloped outer peripheral face 1821.

As illustrated in FIG. 14, a fitting face 1354 of a fitting portion 1035C is parallel to the moving direction. The outer peripheral face 1821 of a rear end-side portion 1082 of the fixation portion 1080C as the end portion of the needle portion 1010 is sloped with respect to the fitting face 1354.

A rear end-side outer diameter d4 of the rear end-side portion 1082 is set to be smaller than an inner diameter d3 of the fitting portion 1035C such that the rear end-side portion 1082 can enter the concave portion 1342 of the cover portion 1034. A distal end-side outer diameter d4 of the rear end-side portion 1082 is set to be larger than the inner diameter d3 of the fitting portion 1035C such that movement of the fixation portion 1080C and accordingly the needle portion 1010 toward the rear end side is restricted.

Although the case where the base portion 1032 and the cover portion 1034 in the case 1030 are separately molded has been described as an example in the aforementioned embodiments and modification example, the present invention is not limited to this configuration, and the base portion 1032 and the cover portion 1034 may be integrally molded as one component.

In addition, although the case where the coil spring is used as the spring 1060 of the movement mechanism 1050 and the coil spring is disposed on the distal end side of the operation portion 1070 has been described as an example, the present invention is not limited to this configuration as long as an energization force for the movement can be applied by an elastic member. For example, a tensile spring may be disposed on the rear end side of the operation portion 1070. In addition, instead of the spring, an elastic member such as a rubber may be used.

Furthermore, although the sloped fitting face (outer peripheral face 1781, fitting face 1351) was provided on either the movement mechanism 1050 or the cover portion 1034 in embodiment 2-1, the sloped fitting face may be provided on both the movement mechanism 1050 and the cover portion 1034. In addition, although the sloped fitting face (outer peripheral face 1821, fitting face 1353) was provided on either the end portion of the needle portion 1010 or the cover portion 1034 in embodiment 2-2, the sloped fitting face may be provided on both the end portion of the needle portion 1010 and the cover portion 1034.

As described above, in order to achieve the second object, the inventions of the medical needles shown in the following (1) to (5) are provided. In the embodiment 2-1, 2-2, and modification example of which, although a winged needle that is used so as to be fixed while piercing the patient's skin has been described as an example, the invention described in (1) to (5) can also be applied to an indwelling needle or the like used for sustained intravenous drip infusion.

(1) A medical needle comprising
a needle portion having a needle tip on a distal end,
a case configured to be capable of exposing the needle portion from the distal end side and accommodating the needle portion, and
a movement mechanism for moving the needle portion inside the case until the needle tip protruding from the case is accommodated in the case, wherein
the case has a base portion having a hole portion through which the needle tip can pass and a cover portion for closing an opening on an opposite side to the hole portion of the base portion,
the cover portion has a fitting portion that is fitted to an end portion of the movement mechanism when the needle portion is moved, and
either the end portion of the movement mechanism or the fitting portion has a fitting face that is sloped so as to gradually decrease in diameter in a moving direction of the needle portion.

(2) The medical needle according to claim 1, wherein the fitting portion has the fitting face to which the end portion of the movement mechanism that moves in association with the movement of the needle portion in a same direction is fitted.

(3) The medical needle according to claim 1 or 2, wherein the movement mechanism comprises an operation portion for moving the needle portion, and
the operation portion moves in association with the movement of the needle portion, and an end portion of the operation portion is fitted to the fitting portion.

(4) A medical needle comprising
a needle portion having a needle tip on a distal end,
a case configured to be capable of exposing the needle portion from the distal end side and accommodating the needle portion, and
a movement mechanism for moving the needle portion inside the case until the needle tip protruding from the case is accommodated in the case, wherein
the case has a base portion having a hole portion through which the needle tip can pass and a cover portion for closing an opening on an opposite side to the hole portion of the base portion,
the cover portion has a fitting portion that is fitted to an end portion of the needle portion that has been moved by the movement mechanism, and
either the end portion of the needle portion or the fitting portion has a fitting face that is sloped so as to gradually decrease in diameter in a moving direction of the needle portion.

(5) The medical needle according to claim 4, wherein the fitting portion has the fitting face to which the end portion of the needle portion is fitted on the basis of the movement of the needle portion.

According to the medical needle described in (1) to (5) above, even if a spring having a relatively strong repulsive force is used as an elastic member, occurrence of impact and noise due to contact between the case and the movement mechanism or the needle portion can be suppressed by the aforementioned sloped fitting face. Thus, the user's discomfort feeling caused when the needle tip is accommodated in the case can be alleviated.

DESCRIPTION OF REFERENCE NUMERALS

1, 1A, 1B, 1C Medical needle
10 Needle portion
30 Case
34 Cover portion
37, 37A, 37B, 37C Movement restricting portion
36 First engagement portion
38 Second engagement portion
39 Third engagement portion
50 Movement mechanism
60 Spring
70 Operation portion
80, 80B Fixation portion 85 Arm
90 Curved portion
1001 Medical needle
1010 Needle portion
1030 Case
1034 Cover portion
1035, 1035A, 1035B, 1035C Fitting portion
1351, 1352, 1353, 1354 Fitting face
1050 Movement mechanism
1060 Spring
1070, 1070A Operation portion
1771, 1781 Outer peripheral face
1080, 1080C Fixation portion
1811, 1821 Outer peripheral face

What is claimed is:

1. A medical needle comprising:
a needle portion having a needle tip on a distal end;
a case configured to be capable of exposing the needle portion to a distal end side and accommodating the needle portion;
a movement mechanism configured to move the needle portion inside the case until the needle tip protruding from the case is accommodated in the case, and including a fixation portion to which the needle portion is attached and an elastic member that energizes the fixation portion in a moving direction of the needle portion; and
a movement restricting portion having an inclined plane that is inclined with respect to the moving direction and configured to restrict the needle tip accommodated in the case from moving in a direction opposite to the moving direction of the needle portion by the movement mechanism, wherein
the movement restricting portion maintains the needle tip accommodated in the case such that the needle tip can come into contact with an inner face of the case, to restrict movement of the needle tip in the opposite direction,
the movement mechanism further includes a spring element provided in a direction crosswise to the moving direction and compressed in the crosswise direction by movement of the fixation portion on the inclined plane, and
the fixation portion is pressed against the inclined plane by the reaction force of the spring element.

2. The medical needle according to claim 1, wherein
the case includes a base portion having a hole portion through which the needle tip can pass, and a cover portion for closing an opening on an opposite side to the hole portion of the base portion, and
the movement restricting portion causes the cover portion to accommodate the needle portion in a direction intersecting the moving direction of the needle portion.

3. The medical needle according to claim 2, wherein
the movement restricting portion maintains the needle tip accommodated in the base portion of the case such that the needle tip can come into contact with an inner face of the base portion.

4. The medical needle according to claim 1, wherein
the movement mechanism further includes an operation portion connected to the fixation portion,
the operation portion has an operation end that is operated to move the fixation portion inside the case until the needle tip protruding from the case is accommodated in the case, and
the operation end comprises the spring element that is compressed in the case by movement of the fixation portion on the inclined plane and presses the fixation portion toward the inclined plane.

5. The medical needle according to claim 1, wherein
the movement mechanism further includes a curved portion that presses the needle portion in an inclined posture back in the opposite direction and presses the needle tip against the inner face of the case.

6. The medical needle according to claim 5, wherein
the movement mechanism further includes an operation portion connected to the fixation portion, and
the curved portion is provided at an end of the operation portion in a moving direction side.

7. The medical needle according to claim 6, wherein
the curved portion is curved so that the curved portion hangs down from an upper position of the end of the operation portion in the moving direction side to an inclined plane side, presses the needle portion in the inclined posture back in the opposite direction and presses the fixation portion against the inner face of the case.

* * * * *